(12) United States Patent
Blodt

(10) Patent No.: US 9,851,235 B2
(45) Date of Patent: Dec. 26, 2017

(54) APPARATUS FOR DETERMINING AND/OR MONITORING AT LEAST ONE PROCESS VARIABLE OF A MEDIUM

(71) Applicant: Endress + Hauser GmbH + Co. KG, Basel (CH)

(72) Inventor: Thomas Blodt, Basel (CH)

(73) Assignee: ENDRESS + HAUSER GMBH + CO. KG, Maulberg (DE)

( * ) Notice: Subject to any disclaimer, the term of this patent is extended or adjusted under 35 U.S.C. 154(b) by 372 days.

(21) Appl. No.: 14/399,211

(22) PCT Filed: Apr. 25, 2013

(86) PCT No.: PCT/EP2013/058574
§ 371 (c)(1),
(2) Date: Nov. 6, 2014

(87) PCT Pub. No.: WO2013/167384
PCT Pub. Date: Nov. 14, 2013

(65) Prior Publication Data
US 2015/0082881 A1 Mar. 26, 2015

(30) Foreign Application Priority Data
May 9, 2012 (DE) ........................ 10 2012 104 075

(51) Int. Cl.
*G01F 23/284* (2006.01)
*G01N 9/24* (2006.01)
*G01F 23/26* (2006.01)

(52) U.S. Cl.
CPC ............. *G01F 23/284* (2013.01); *G01N 9/24* (2013.01); *G01F 23/268* (2013.01)

(58) Field of Classification Search
CPC ...... G01F 23/284; G01F 23/268; G01S 13/88; G01S 7/032; G01N 22/00; G01N 9/24
See application file for complete search history.

(56) References Cited

U.S. PATENT DOCUMENTS

| 5,043,707 A | 8/1991 | Heinze |
| 7,730,780 B2 | 6/2010 | Neven |

(Continued)

FOREIGN PATENT DOCUMENTS

| CN | 1874066 A | 12/2006 |
| CN | 101305495 A | 11/2008 |

(Continued)

OTHER PUBLICATIONS

English Language Machine Translation of DE 19934041 A1. Translation dated Nov. 16, 2016. Accessed online at <http://translationportal.epo.org/>.*

(Continued)

*Primary Examiner* — Lisa Caputo
*Assistant Examiner* — Punam Roy
(74) *Attorney, Agent, or Firm* — Bacon & Thomas, PLLC

(57) ABSTRACT

An apparatus for determining and/or monitoring at least one process variable of a medium in a container or pipeline, including a resonator, which is in contact with an interior of the container or the pipeline, an active element for producing a high-frequency signal in the resonator and an electronics unit, which is embodied to receive from a unit formed of the resonator and the active element an electrical output signal. The electrical output signal is evaluated with reference to frequency.

9 Claims, 3 Drawing Sheets

(56) References Cited

U.S. PATENT DOCUMENTS

| | | |
|---|---|---|
| 8,085,156 B2 | 12/2011 | Schumacher |
| 8,125,391 B2 | 2/2012 | Knudsen |
| 2004/0056667 A1* | 3/2004 | Lutke .................. G01F 23/284 |
| | | 324/644 |
| 2009/0126483 A1* | 5/2009 | Blendinger ........... G01F 23/246 |
| | | 73/304 C |

FOREIGN PATENT DOCUMENTS

| | | |
|---|---|---|
| CN | 101794934 A | 8/2010 |
| DE | 3044353 A1 | 6/1982 |
| DE | 3044353 C2 | 6/1982 |
| DE | 4040084 A1 | 6/1992 |
| DE | 19516789 A1 | 11/1996 |
| DE | 19614286 C1 | 9/1997 |
| DE | 19807593 A1 | 2/1999 |
| DE | 19934041 A1 | 3/2001 |
| DE | 10051025 A1 | 4/2002 |
| DE | 102004060338 A1 | 7/2006 |
| DE | 102005054233 A1 | 5/2007 |
| DE | 102007007407 A1 | 8/2008 |
| DE | 102007042954 A1 | 3/2009 |
| EP | 0361023 A1 | 4/1990 |
| EP | 2031416 B1 | 3/2009 |
| GB | 1405003 A * | 9/1975 ........... G01F 23/284 |

OTHER PUBLICATIONS

German Search Report, German PTO, Munich, dated Jan. 22, 2013.
International Search Report, EPO, The Netherlands, dated Sep. 17, 2013.
English Translation of the International Preliminary Report on Patentability, WIPO, Geneva, CH, dated Nov. 20, 2014.

* cited by examiner

APPARATUS FOR DETERMINING AND/OR MONITORING AT LEAST ONE PROCESS VARIABLE OF A MEDIUM

TECHNICAL FIELD

The present invention relates to an apparatus for determining and/or monitoring at least one process variable of a medium in a container or pipeline. The medium is present as a fine-grained or powdered, bulk good or as a fluid, especially in the form of a gas or a liquid. The process variable is the fill level or the dielectric constant of a medium. The fill level can be a continuous fill level of a medium, a predetermined limit-level of a medium, or the limit-level of an interface between two media.

BACKGROUND DISCUSSION

A number of different measuring principles exist for fill level measurement. Vibronic limit level switches use a mechanically oscillatable unit, for example, in the form of a rod or a fork, which is placed at a fill level height to be monitored in a container and excited to execute resonant, mechanical oscillations. The frequency of the oscillations depends on whether the oscillatable unit is oscillating in air or covered by a liquid medium. A frequency change indicates, consequently, the reaching of the limit level. For detection of bulk goods, as a rule, a monitoring of the oscillation amplitude is used.

Another type of fill-level measuring device is based on the capacitive principle. In such case, a probe electrode is supplied with an alternating voltage signal and the capacitance between the probe electrode and the container wall or a second electrode is determined. For limit level measurement, also a coaxial arrangement of probe- and ground electrode is known for introduction through a wall of the container.

Especially for continuous fill level measurement in containers, further known are so called TDR probes. Such sensors operate according to a principle involving measuring the travel time of electromagnetic signals, which propagate along a waveguide protruding into the medium and are reflected at the interface of the medium. Such sensors are strongly susceptible to high-frequency disturbance signals. Known from Offenlegungsschrift DE 20016962 U1 is a limit level switch, which utilizes the TDR principle.

SUMMARY OF THE INVENTION

An object of the invention is to provide an apparatus that is resistant to the in-coupling of disturbance signals and can determine at least one limit-level of a medium in a manner different from the state of the art.

The object is achieved by an apparatus having a resonator, which is in contact with an interior of the container or pipeline, an active element for producing a high-frequency signal in the resonator and an electronics unit, which is embodied to receive from the unit formed of resonator and active element an electrical output signal and to evaluate the output signal with reference to frequency.

The terminology, high-frequency signal, means a signal with a frequency in the region of some 10 s of MHz to some 10 s of GHz or higher. Preferably, it is a microwave signal. Preferably, the frequency of the transmission signal lies in the S-, C-, X-, or K-band, i.e. between 2.4 and 26 GHz. However, also lesser frequencies, for example, 40 or 800 MHz, or higher frequencies, provide options. The frequency depends, in such case, on the structure and dimensioning of the resonator.

The resonator is, for example, part of a reflex oscillator. Besides the resonator, the oscillator includes an active element, for example, in the form of an amplifier, for producing and in-coupling an oscillation into the resonator and an out-coupling element for out-coupling an output signal. The output signal of the resonator possesses the same frequency as the input signal and is supplied to an electronics unit for evaluation. The frequency of the output signal depends on the medium, with which the resonator is in contact. The embodiment of the contact surface depends, in such case, on the embodiment of the resonator. If the medium, which with the resonator is in contact, changes, then the frequency of the wave propagating in the resonator changes. The frequency change depends, in such case, on the dielectric constant of the medium. Besides the fill level of a medium, frequency can also be used to determine the dielectric constant of a medium.

The apparatus of the invention differs from apparatuses known from the state of the art for fill level measurement by means of high frequency technology especially by the feature that the medium directly influences the signal production. The resonator forms the sensor. In contrast to capacitive probes, only a very small signal propagation occurs in the process, i.e. in the interior of the container or pipeline.

In a first embodiment, the resonator is embodied as a hollow conductor or as a coaxial probe, with an inner conductor and an outer conductor coaxially surrounding the inner conductor. The hollow conductor is, for example, a round, hollow conductor or a rectangular, hollow conductor. The hollow conductor, respectively the coaxial probe, can, in such case, be filled with air or with a dielectric in the form of a solid, wherein the dielectric preferably has a high dielectric constant in the order of magnitude of 3 to 8, especially 4. It can also be a miniature surge pipe, into which the medium can penetrate. A resonator embodied as a hollow conductor or coaxial probe has a contact surface bounding the interior of the container or pipeline and oriented perpendicular to the propagation direction of the wave in the resonator. The wave is reflected at this contact surface.

In an alternative embodiment, the resonator is embodied as a microstrip transmission line or as a patch antenna. The microstrip transmission line is, for example, open or provided with a short circuit, in order to bring about a reflection. The microstrip transmission line is arranged in such a manner that the fields of the wave propagating in the microstrip transmission line extend partially into the interior of the container or pipeline.

In an embodiment, the resonator at least sectionally bounds the interior of the container or pipeline via interpositioning of an electrically insulating, process isolating layer. The process isolating layer is embodied, for example, as a membrane of PTFE. For the case, in which the resonator is embodied as a hollow conductor filled with a dielectric or a coaxial probe filled with a dielectric, the process isolating layer is composed preferably of a material, whose dielectric constant corresponds at most to the dielectric constant of the dielectric material of the resonator.

In an embodiment of the invention, the electronics unit includes a mixer for converting the output signal into a low-frequency signal. The mixer produces from the high-frequency output signal and a reference signal with constant frequency a signal with a lower frequency, which equals, for example, the difference between the two signals. Serving for the production of the reference signal is, for example, a voltage controlled oscillator or an oscillator constructed analogously to the oscillator comprising the sensor. The low frequency signal is suppliable to an analog or digital evaluation unit for frequency determination.

A further development provides that there is arranged neighboring the resonator a second resonator, which does not contact the medium and serves for producing a reference signal, and that the mixer produces a temperature compensated signal from the output signal and the reference signal. The second resonator is arranged neighboring the first resonator serving as sensor, so that the two resonators are exposed to the same ambient temperature and exhibit the same temperature behavior. By mixing the output signal of the oscillator with the signal of the second resonator, a signal is produced, in which temperature related frequency changes are compensated.

In another embodiment, the electronics unit includes a filter, which is fed the output signal, and which is designed in such a manner that the amplitude of the output signal of the filter exhibits a unique dependence on the frequency of the output signal of the oscillator. From the unique frequency dependence of the amplitude, the frequency of the output signal is determinable based on amplitude.

In an embodiment, the electronics unit is embodied to detect a change of the frequency of the output signal and based on the change to detect a change of a limit level of the medium. The value of the frequency does not have to be determined absolutely in this embodiment. The electronics unit detects only a change of the frequency and is correspondingly simply embodiable. Such an apparatus provides a cost effective, limit level switch.

In an advantageous further development of the invention, furnished in the electronics unit is at least one limit value for the frequency of the output signal, and the electronics unit is embodied to compare the frequency of the output signal with the limit value and to produce an alarm signal, when the frequency reaches the limit value. The apparatus permits monitoring of a limit-level of a medium and further can distinguish between different media, so that also the interface between two media is determinable. If the media are known, a limit value for the frequency can be furnished for each medium. In this way, an alarm signal is producible, when the medium to be detected contacts the resonator.

In an embodiment, the electronics unit is embodied to determine the frequency of the output signal and to figure from that a dielectric constant of the medium. For example, corresponding relationships between frequency and dielectric constant are furnished in a memory unit, which can also be part of a digital processing unit, for example, a microcontroller.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
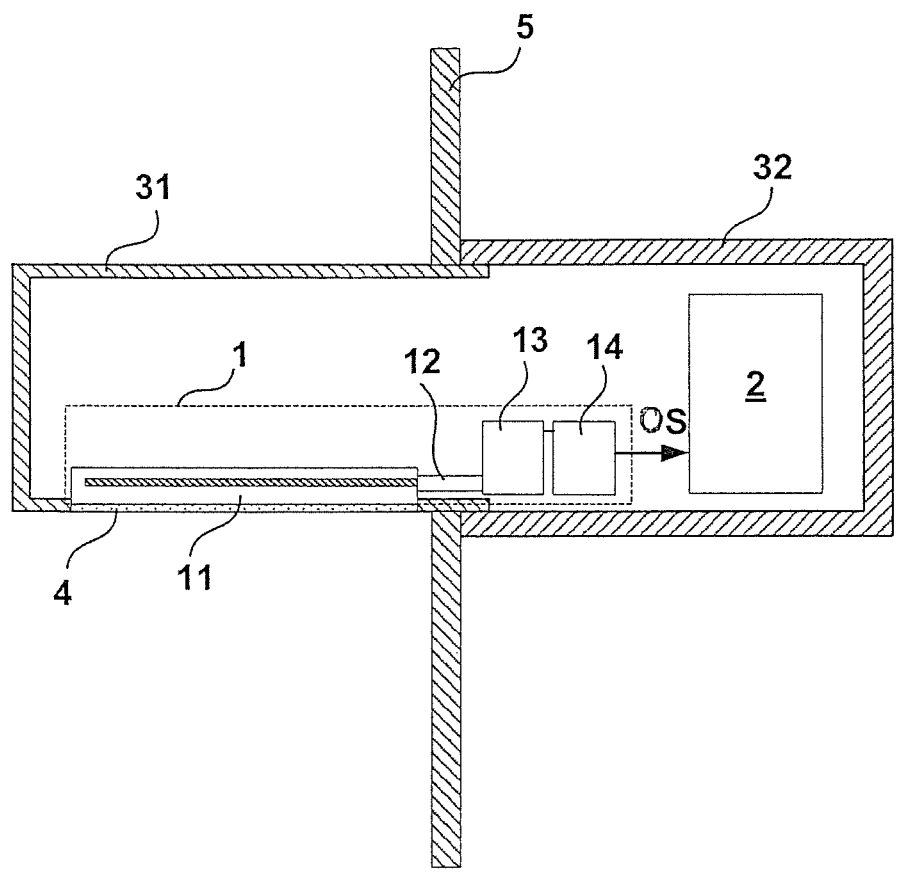
FIG. 1 is a schematic representation of an apparatus mounted in a container wall and having a microstrip transmission line as resonator.

FIG. 1 shows schematically an advantageous embodiment of an apparatus of the invention mounted in a container 5. Container 5 is indicated in the representation by a part of a wall. Located in the interior of the container 5 as sensor is the resonator 11 of an oscillator 1. The resonator 11 is for mechanical protection placed in a sensor housing 31, which is mounted in an opening in the wall of the container 5, for example, via a threaded screw-in mounting or a flange. An embodiment without sensor housing 31 is, however, likewise possible.

Via a plugged connection 12 suitable for transmission of high-frequency signals, the resonator 11 is connected with the remaining components of the oscillator 1, which are arranged outside of the container 5 in a field housing 32. These components include an active element for producing and maintaining an oscillation in the resonator 11 and an out-coupling element 14 for out-coupling a part of the oscillations from the resonator 11 via the active element 13. The out-coupled part of the oscillations forms the output signal OS of the oscillator 1. The plugged connection 12 can be a simple plugged connection between two similar waveguides or a connecting element between two differently embodied waveguides. A connection between different types of waveguides is required, for example, when the active element 13 is arranged on a microstrip transmission line or on a circuit card, while the resonator 11, in contrast, is embodied as a hollow conductor or coaxial probe. A direct connecting of the resonator 11 to the active element 13 is likewise possible, in which case the plugged connection 12 is absent.

The output signal OS is fed to an electronics unit 2 likewise arranged in the field housing 32. Electronics unit 2 evaluates the output signal OS with reference to frequency and determines the process variable based on the frequency. The embodiment of the electronics unit 2 and the evaluation of the output signal OS will be explored in greater detail in connection with the discussion of FIGS. 3a and 3b. The process variable can be queried or output via an interface.

Active element 13 produces the oscillation in interaction with the resonator 11 either continuously or pulse like. A pulse operation is energy saving compared with continuous operation. The pulse length is, in such case, specified in such a manner that the pulse length is greater than the product of oscillation duration and quality. Suited as active element 13 is, for example, a Gunn diode or a transistor. Active element 13 can also have a hollow conductor construction. The frequency of the produced oscillations lies preferably in the gigahertz range, for example, between 2.4 and 26 GHz.

Applicable as out-coupling element 14 are, for example, amplifiers, capacitors, transformers or so called line elements for high frequencies from about 1 GHz in the form of filter structures or laterally coupled, line pairs. Optionally, the out-coupling element 14 includes a limiter amplifier or a limiter amplifier is arranged after the out-coupling element 14.

In the illustrated example of an embodiment, the resonator 11 is embodied as an open microstrip transmission line. Instead of an open microstrip transmission line, also suitable is a microstrip transmission line equipped with a short circuit. The microstrip transmission line includes one or more conductive strips applied on a dielectric. The side of the dielectric material facing away from the at least one strip is provided with a metal coating. The microstrip transmission line is mounted in the sensor housing 31 in such a manner that the metal coating faces the interior of the sensor housing 31. The sensor housing 31 includes a window, so that the at least one strip has at least sectionally direct contact with the interior of the container 5 and is not surrounded by the sensor housing 31. Advantageous is an embodiment, in which the window is covered with a process isolating layer 4 of an electrically insulating material. The process isolating layer 4 can also be applied in the form of a thin layer directly on the conductive strip. For example, the process isolating layer 4 is composed of PTFE or a PTFE derivative, for example, ETFE.

In another embodiment, the resonator 11 is a patch antenna, preferably of low quality. A patch antenna includes at least one resonator, which, as a rule, is formed by one or more plies of a metal coating applied on a circuit board and a grounding surface on the oppositely lying side of the circuit board. Because of the low quality, only a small part of the power of the patch antenna is radiated and the frequency change in the case of a change of the limit level is higher than in the case of a patch antenna with high quality. The terminology, low quality, means a quality up to about 100. Especially suitable for use in an apparatus of the invention is a patch antenna with a very low quality of less than 20, for example, between 5 and 20. The connection between patch antenna and active element 13 is produced via a waveguide, for example, a microstrip transmission line or a coaxial line.

In another embodiment, the resonator 11 is embodied as a hollow conductor. The hollow conductor can be, for example, of round or rectangular cross section and includes a metal wall. Another form of embodiment of the resonator 11 is a coaxial probe with an inner conductor and an outer conductor 16, which coaxially surrounds the inner conductor 15 to form an intermediate space. In a variant, the intermediate space of the coaxial probe or the hollow space of the hollow conductor is filled with a dielectric in the form of a solid, for example, PTFE. A coaxial probe is equally suitable as resonator 11 for high and low frequencies. The end region of the hollow conductor, respectively the coaxial probe, is preferably sealed with a process isolating layer 4, so that a contact surface to the medium is formed directed perpendicular to the metal wall of the hollow conductor, respectively the coaxial probe. Especially for the case of a resonator 11 filled with a dielectric in the form of a solid, a process isolating layer 4 can also be omitted. Essential is that there is a nonmetal contact surface to the interior of the container 5 and, in given cases, to the medium located therein, so that the medium can influence the frequency of the oscillation propagating in the resonator 11. The resonator 11 can protrude into the interior of the container 5 or be arranged in such a manner that the contact surface seals flushly with the inner wall of the container 5.

In a variant of a hollow conductor or coaxial probe, the wall, respectively the outer conductor, of the resonator 11 is formed by a sounding tube, which preferably has a diameter of some millimeters and a length of 1 to several centimeters, for example, 1-20 cm, especially 1-10 cm. A process isolating layer is not present, so that the medium can penetrate into the sounding tube. Especially in small containers 5 with a height of 10-20 cm, a resonator 11 embodied in such a manner permits, in the case of vertical installation, continuous determination of fill level, since a frequency change corresponding to the rise height of the medium in the sounding tube results.

According to the invention, the resonator 11 forms the sensor for the medium to be detected. The frequency of the signal traveling back and forth in the resonator 11 depends on the medium, more exactly stated on the dielectric constant of the medium, which with the resonator 11 is in direct contact. In an embodiment with a process isolating layer 4, in such case, the medium in contact with the process isolating layer 4 is decisive for the oscillation frequency. In the case of a change of the degree of coverage, there occurs within a certain period of time an adapting of the oscillations in the resonator 11 to the changed boundary conditions. This period of time is given by the product of the quality of the resonator 11 and the oscillation period of the oscillations with the adapted frequency. Resonator 11 is preferably designed in such a manner that the oscillator 1 has a quality between 1 and 100.

Because of the small wave propagation and the narrow frequency band of the oscillator 1, the apparatus of the invention has a high disturbance resistance against disturbance signals.

Not only the monitoring of a limit level is possible with the apparatus of the invention. After corresponding training, a frequency of the output signal OS can be associated with a certain medium, respectively a certain dielectric constant. In this way, the medium contacting the resonator 11 can be determined, or an interface between two media, for example, water and oil, can be detected. For use as a limit level switch, no adjusting on-site is required, so that the apparatus can be placed in operation directly after mounting. Furthermore, continuous fill level measurement is possible in containers 5 having small dimensions. For this, however, the dielectric constant and/or the electrical conductivity of the medium to be detected should be known. The fill level is determinable from the frequency of the output signal OS of the oscillator by means of a characteristic curve evaluation.

Advantageous, moreover, is an integration of the oscillator 1 into a capacitive measuring probe for flush mounted installation in a wall of a container 5 or pipeline 6. A measuring device with such a capacitive measuring probe is produced and sold by the applicant under the mark, LIQUIPOINT M. Because of the, compared to a capacitive measuring, smaller propagation of the electromagnetic field into the interior of the container 5 or pipeline 6, oscillator 1 can measure also in structures of smaller dimensions, where measurement based on the capacitive principle would be disturbed, because of the small distance to the oppositely lying wall. The integration of the oscillator 1 into the capacitive measuring probe leads, consequently, to an increase in the number of situations, in which the measuring device can be applied.

Figure 2:
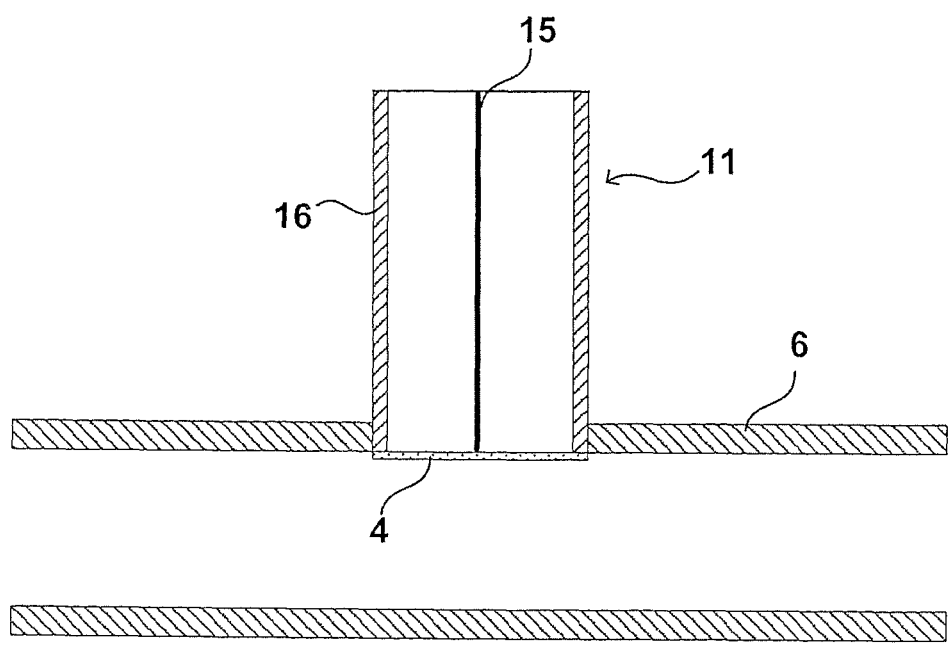
FIG. 2 is a schematic representation of an apparatus mounted in a pipeline and having a coaxial probe as resonator.

FIG. 2 discloses in schematic representation an apparatus of the invention mounted in a pipeline 6. Resonator 11 is here arranged outside of the process. Such an embodiment is suited especially for pipelines 6 with small diameter or also for containments with small dimensions, for example, so called bio bags, which are single-use containers for accommodating biological material and for carrying out chemical reactions. Resonator 11 is embodied as a coaxial probe, which is isolated from the interior of the pipeline 6 by a process isolating layer. The coaxial probe includes an inner conductor 15, which is coaxially surrounded by an outer conductor 16. The intermediate space is filled by a dielectric. The dielectric is, for example, air or PTFE. In the former case, there is, for example, an air exchange between the intermediate space and the inner space of the field housing 32, in which the electronics unit 2 is located. Advantageous is a dielectric, whose dielectric constant is greater than that of the medium to be detected in the pipeline 6. In the case of a metal pipeline 6, the outer conductor can be electrically connected with the pipeline.

The process isolating layer 4 is essentially flush with the pipeline 6. The material of the process isolating layer 4 is selected from the electrically insulating materials preferably in such a manner that its dielectric constant is at most equal to the dielectric constant of the dielectric material located between inner conductor 15 and outer conductor 16. Preferably, it is further a stable material, which is not removed by a flow reigning, in given cases, in the pipeline 6. A suitable material is, for example, a PTFE derivative, especially ETFE.

Advantageous in the case of this embodiment is, among other things, that the separation of inner conductor 15 and outer conductor 16 can be very small, this meaning thus a coaxial probe of small diameter is created, which is suited for installation in pipelines 6 of small nominal diameter. Furthermore, the coaxial probe has a flat end region, which protrudes scarcely into the interior of the pipeline 6 and, thus, provides very little resistance, if at all, to the flow of the medium.

Instead of the coaxial probe, also a hollow conductor, a microstrip transmission line, or a patch antenna of low quality is suitable as resonator 11 for use in a pipeline 6 of small nominal diameter.

Figure 3A:
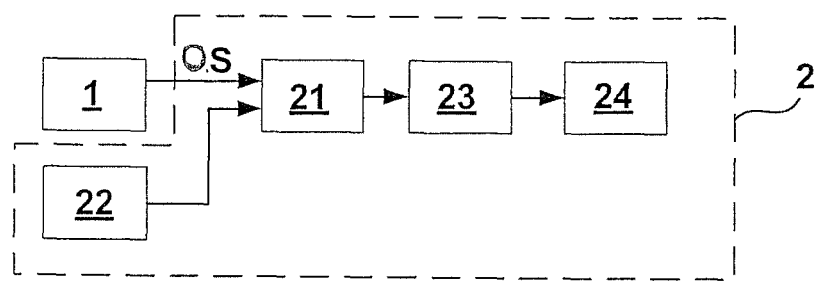
FIG. 3a is a block diagram of a first embodiment of the electronics unit.
Figure 3B:
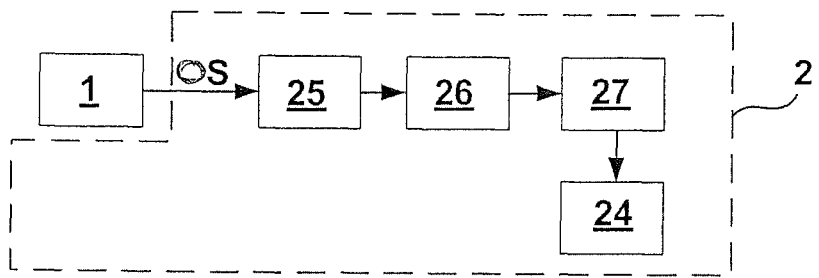
FIG. 3b is a block diagram of a second embodiment of the electronics unit.

FIGS. 3a and 3b show block diagrams of two examples of embodiments for an electronics unit 2 of an apparatus of the invention. In each case, the electronics unit 2 is fed the output signal OS of the oscillator 1.

FIG. 3a shows an evaluation based on frequency. For this, the output signal OS is fed to a first input of a high frequency mixer 21. Applied to a second input of the high frequency mixer 21 is a reference signal of constant frequency. The high frequency mixer 21 functions to shift the frequency of the output signal OS of the oscillator 1 to a lower frequency by difference forming with the reference signal. Signals with low frequencies are more easily and cost effectively further processable than high-frequency signals. The lower frequency can also be almost zero, so that a change of the oscillations in the resonator 11 is recognizable by occurrence of a frequency different from zero at the output of the high frequency mixer 21. The high-frequency mixer 21 comprises, for example, one or more diodes or a Gunn element, or it is composed of transistors, especially in the form of a Gilbert cell.

The frequency of the output signal OS assumes values in a frequency range bounded by a lower and an upper limit frequency. The reference oscillator 22 is preferably embodied in such a manner that the frequency of the reference signal at least essentially corresponds to the upper limit frequency or the lower limit frequency. The signal on the output of the high frequency mixer 21 assumes then values, which lie between 0 Hz and an upper value, which corresponds to the width of the frequency range.

The reference signal is produced by a reference oscillator 22. For example, the reference oscillator 22 is a voltage controlled oscillator, also known under the acronym VCO. The frequency of a VCO is electronically tunable. Alternatively, the reference oscillator 22 is constructed analogously to the oscillator 1 serving for measuring and producing the output signal OS. Such a reference oscillator 22 includes an active element for producing an oscillation, a frequency determining element, an out-coupling element and preferably a limiter amplifier. The frequency determining element can be embodied as a mechanically tunable resonator, for example, in the form of a microstrip transmission line, or as an electronically tunable component, for example, as a varactor diode. In an embodiment, the active element is a field effect transistor. Via the frequency determining element, which is present in the circuitry of the field effect transistor, the oscillation characteristics, especially the oscillation frequency, are adjustable.

If the apparatus is applied in an environment, in which extreme temperatures or large temperature jumps occur, the frequency of the oscillations in the resonator 11 can have a temperature dependence. This can be compensated by embodying the resonator of the reference oscillator 22 and the resonator 11 of the oscillator 1 essentially equally, for example, both as coaxial probes, and arranging them as neighbors, so that they are exposed to the same temperature. Furthermore, the active elements for oscillation production should be embodied equally. The resonator of the reference oscillator 22 is not in contact with the medium or else it has a metal interface with such, so that the frequency of the reference signal produced by means of the reference oscillator 22 is not influenced by the medium. Alternatively, an electronic temperature compensation is possible. For this, a temperature sensor measures the temperature reigning at the site of the resonator 11 and, by means of a furnished temperature dependence of the frequency of the output signal OS, an evaluation unit, for example, the microcontroller 24, provides a corresponding correction of the frequency.

The low frequency output signal of the high frequency mixer 21 is fed to a frequency counter 23, wherein there can be a filter between the mixer 21 and the frequency counter 23. The frequency counter 23 determines the frequency of the processed signal, from which, using the known conversion by the high-frequency mixer 21, the frequency of the output signal OS of the oscillator 1 is determinable. The signal of the frequency counter 23 is fed to a digital processing unit in the form of a microcontroller 24. For limit-level monitoring, the microcontroller 24 compares the ascertained frequency of the output signal OS with a furnished limit value, whose exceeding or subceeding corresponds to the reaching of the limit level to be monitored. Microcontroller 24 produces a corresponding switch signal, which indicates whether the limit-level has been reached. In another variant, the switch signal is produced with analog components. Alternatively to the frequency determination by means of the frequency counter 23, the frequency is also determinable by the microcontroller 24. For this, the output signal of the high frequency mixer 21 is fed to an analog-digital converter and the digitized signal to the microcontroller 24.

FIG. 3b shows the output signal OS fed via a limiter amplifier 25 to a high frequency filter 26. The limiter amplifier 25 amplifies the high-frequency signal up to an internal saturation point of the output amplitude and serves for compensating a small frequency response of the oscillator 1. The limiter amplifier 25 is an optional component of this embodiment. The high frequency filter 26 is designed in such a manner that the amplitude of the filtered signal is frequency dependent and, in such case, at least within a predetermined frequency band, uniquely related to frequency. The predetermined frequency band contains at least all those frequencies, which the output signal OS can have. In this way, each frequency of the output signal OS of the oscillator 1 bears a different amplitude, so that frequency can be uniquely determined from amplitude. The high frequency filter 26 is embodied, for example, as a highpass or lowpass filter.

The filtered output signal is fed to a detector 27, which determines amplitude of the filtered output signal. The detector 27 is, for example, a high-frequency diode or a thermal high-frequency detector.

The associating of voltage amplitude to frequency of the output signal OS of the oscillator 1 is stored, for example, in a microcontroller. The signal applied on the output of the detector 27 is fed after analog-digital conversion to the microcontroller 24 for evaluation. The production of the switch signal occurs as described in connection with FIG. 3*a*.

In an additional embodiment (not shown) of the electronics unit 2, the output signal OS of the oscillator 1 is fed directly to a frequency counter. The frequency counter is a circuit arrangement embodied in analog technology for determining the frequency of a signal. This embodiment, is especially suitable for relatively low frequencies below 2.4 GHz.

The invention claimed is:

1. An apparatus for determining and/or monitoring a limit level or a dielectric constant of a medium in a container or pipeline, comprising:
   a resonator, which is in contact with the medium;
   an active element for producing a high-frequency signal in said resonator; and
   an electronics unit, which is embodied to receive from a unit formed of said resonator and said active element an electrical output signal, and to evaluate the output signal with reference to frequency,
   characterized in that the electronics unit is embodied to determine the frequency of the output signal and to figure from the frequency, the dielectric constant of the medium, and/or
   the electronics unit is embodied to detect a change of the frequency of the output signal and based on the change to detect a change of the limit level of the medium,
   wherein said resonator at least sectionally bounds the interior of the container or pipeline via interpositioning of an electrically insulating, process isolating layer.

2. The apparatus as claimed in claim 1, wherein:
   said resonator is embodied as a hollow conductor or as a coaxial probe, with an inner conductor and an outer conductor coaxially surrounding said inner conductor.

3. The apparatus as claimed in claim 1, wherein:
   said resonator is embodied as a microstrip transmission line or as a patch antenna.

4. The apparatus as claimed in claim 1, wherein:
   said electronics unit includes a mixer for converting the output signal into a low-frequency signal.

5. The apparatus as claimed in claim 4, further comprising:
   a second resonator arranged neighboring said resonator, which does not contact the medium and which serves for producing a reference signal; and
   said mixer produces a temperature compensated signal from said output signal and said reference signal.

6. The apparatus as claimed in claim 1, wherein:
   said electronics unit includes a filter, which is fed said output signal, and which is designed in such a manner that the amplitude of said output signal of said filter is uniquely related to the frequency of said output signal of said oscillator.

7. The apparatus as claimed in claim 1, wherein:
   said electronics unit is embodied to detect a change of the frequency of said output signal and based on the change to detect the change of the limit level of the medium.

8. The apparatus as claimed in claim 1, wherein:
   furnished in said electronics unit is at least one limit value for the frequency of said output signal; and
   said electronics unit is embodied to compare the frequency of said output signal with the limit value and to produce an alarm signal, when the frequency reaches the limit value.

9. The apparatus as claimed in claim 1, wherein:
   said electronics unit is embodied to determine the frequency of said output signal and to figure from that the dielectric constant of the medium.

* * * * *